United States Patent
Chun

(10) Patent No.: US 10,106,840 B2
(45) Date of Patent: Oct. 23, 2018

(54) QUANTIFICATION OF TARGET NUCLEIC ACID USING MELTING PEAK ANALYSIS

(71) Applicant: SEEGENE, INC., Seoul (KR)

(72) Inventor: Jong Yoon Chun, Seoul (KR)

(73) Assignee: SEEGENE, INC., Seoul (KR)

( * ) Notice: Subject to any disclaimer, the term of this patent is extended or adjusted under 35 U.S.C. 154(b) by 293 days.

(21) Appl. No.: 14/773,859

(22) PCT Filed: Mar. 13, 2014

(86) PCT No.: PCT/KR2014/002116
§ 371 (c)(1),
(2) Date: Sep. 9, 2015

(87) PCT Pub. No.: WO2014/142575
PCT Pub. Date: Sep. 18, 2014

(65) Prior Publication Data
US 2016/0068892 A1    Mar. 10, 2016

(30) Foreign Application Priority Data

Mar. 13, 2013  (KR) .................. 10-2013-0026837

(51) Int. Cl.
*C12Q 1/68* (2018.01)
*C12Q 1/6851* (2018.01)
*C12Q 1/6818* (2018.01)

(52) U.S. Cl.
CPC ......... *C12Q 1/6851* (2013.01); *C12Q 1/6818* (2013.01)

(58) Field of Classification Search
CPC combination set(s) only.
See application file for complete search history.

(56) References Cited

U.S. PATENT DOCUMENTS

| 6,174,670 B1 | 1/2001 | Wittwer et al. |
| 6,245,514 B1 | 6/2001 | Wittwer |
| 2010/0233686 A1 | 9/2010 | Higuchi et al. |
| 2010/0285468 A1 | 11/2010 | Xin |

FOREIGN PATENT DOCUMENTS

| CN | 102827939 A | 12/2012 | |
| EP | 1288314 A2 | 3/2003 | |
| WO | WO-2011158037 A2 * | 12/2011 | ........... C12Q 1/6806 |
| WO | 2012096430 A1 | 7/2012 | |

OTHER PUBLICATIONS

Al-Robaiy, Samiya, et al., Rapid Competitive PCR Using Melting Curve Analysis for DNA Quantificaiton, BioTechniques, vol. 31, No. 6, pp. 1382-1388, Dec. 2001, Leipzig, Germany.

Lyon, Elaine, et al., Quantification of HER2/neu Gene Amplification by Competitive PCR Using Fluorescent Melting Curve Analysis, Clinical Chemistry, vol. 47, No. 5, pp. 844-851, 2001.

* cited by examiner

*Primary Examiner* — Samuel C Woolwine
(74) *Attorney, Agent, or Firm* — Gianna J. Arnold; Saul Ewing Arnstein & Lehr LLP

(57) ABSTRACT

The present invention relates to a method for quantifying a target nucleic acid sequence performed in such a manner that at least two cycles in the nucleic acid amplification subject to melting peak analysis are predetermined before the nucleic acid amplification and melting peak analyses are performed for the at least two predetermined cycles, followed by quantifying the target nucleic acid sequence using data values from the melting peak curve (e.g., the presence or absence, height and area).

16 Claims, No Drawings
Specification includes a Sequence Listing.

QUANTIFICATION OF TARGET NUCLEIC ACID USING MELTING PEAK ANALYSIS

CROSS REFERENCE TO RELATED APPLICATIONS

This application claims the priority of PCT/KR2014/002116, filed on Mar. 13, 2014, which claims priority to Korean Patent Application No. 10-2013-0026837, filed Mar. 13, 2013, the entire contents of each of which are hereby incorporated in total by reference.

SEQUENCE LISTING

This application incorporates by reference the Sequence Listing contained in an ASCII text file named "361406-00025_SeqList.txt" submitted via EFS-Web. The text file was created on Sep. 8, 2015, and is 2 kb in size.

BACKGROUND OF THE INVENTION

Field of the Invention

The present invention relates to a method for quantifying a target nucleic acid sequence by use of a melting analysis.

Description of the Related Art

A target nucleic acid amplification process is prevalently involved in most of technologies for detecting target nucleic acid sequences. Nucleic acid amplification is a pivotal process for a wide variety of methods in molecular biology, such that various amplification methods have been proposed.

The most predominant process for nucleic acid amplification known as polymerase chain reaction (hereinafter referred to as "PCR") is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al., (1985) Science 230, 1350-1354).

As alternatives, various methods such as LCR (Ligase Chain Reaction), DA (Strand Displacement Amplification), NASBA (Nucleic Acid Sequence-Based Amplification), TMA (Transcription Mediated Amplification) and RCA (Rolling-Circle Amplification) have been suggested.

As application of nucleic acid amplification to target detection, the real-time detection methods are widely utilized to detect a target sequence with measuring nucleic acid amplification in a real-time manner.

The real-time detection methods generally use labeled probes specifically hybridized with target sequences. As examples of methods using hybridization between labeled probes and target sequences, the Molecular beacon method using dual-labeled probes capable of hairpin structure (Tyagi et al, *Nature Biotechnology* v. 14 Mar. 1996), the Hybridization probe method using two probes singly labeled with donor or acceptor (Bernad et al, 147-148 *Clin Chem* 2000; 46) and the Lux method using single-labeled oligonucleotides (U.S. Pat. No. 7,537,886) have been developed. In addition, the TaqMan method using cleavage reaction of a dual-labeled probe by the 5'-nuclease activity of DNA polymerases as well as hybridization of dual-labeled probes has been widely employed (U.S. Pat. Nos. 5,210,015 and 5,538,848).

In the real-time detection methods as homogenous assay, the amplification and detection analysis are performed in a single tube such their performance is relatively convenient. In addition, the real-time detection methods are free from contaminations. However, for simultaneous detection of a plurality of target sequences in a real-time manner, there is limitation not only in utilization fluorescent molecules due to assignment of a fluorescent molecule to a target nucleic acid molecule but also in detectable target number per sample due to spectrum interference between fluorescent molecules.

As alternatives for target detection in a homogenous assay, the post-PCR melting assay has been suggested in which fluorescent intensities are monitored with increasing or decreasing in a temperature range after target amplification and then amplicons are detected using the melting profile.

U.S. Pat. No. 5,871,908 and U.S. Pat. No. 6,174,670 disclose target detection methods by melting analysis of target sequences in a double strand or duplex between target sequence and probe. WO 2012/096523 discloses a melting analysis of extended duplexes formed dependent on the presence of target sequences. This method that does not use target sequences for melting analysis forms extended duplexes having pre-selected sequences when the target sequence is present, which renders a melting analysis to be performed in more effective manner.

Because the methods using a melting analysis utilizes melting temperatures particular to duplexes, they have advantages in which a plurality of target sequences are simultaneously detected by use of a single type of fluorescent label (see U.S. Pat. No. 8,039,215).

In the meantime, the quantification of target sequences as well as target detection is usually required for prognosis determination and analysis of drug responsiveness in the diagnostic field.

The real-time PCR assay is used to quantify target sequences by use of standard quantification curve and $C_t$ (threshold cycle) value. The amplification curves are obtained for standard materials prepared by serious dilution of target sequences with known concentration, and the standard quantification curve is then plotted using the log values of initial amounts of standard materials and $C_t$ values. The $C_t$ value of unknown sample is obtained by real-time PCR and then quantified using the standard quantification curve. Although the quantification method is relatively convenient, it has serious problems due to loss in sample extraction step and PCR inhibition. For overcoming such problems, a quantification method using internal control has been suggested.

The post-PCR melting assay has been applied to quantification by use of height or area of melting peaks.

For example, U.S. Pat. No. 6,245,514 describes that a target sequence and a nucleic acid molecule with known concentration (reference template) are amplified in the presence of nucleic-acid-binding fluorescent dye, melting peaks for amplification products are obtained and integrated to determine relative amounts of the target sequence and the reference template, thereby calculating concentration of the target sequence. The target sequence and the reference template can be differentially detected because they have different $T_m$ values from each other. U.S. Pat. No. 6,174,670 discloses a quantification method using hybridization probes and melting peaks. Since the methods described above performs a melting analysis after target amplification, they have disadvantages in that quantification results are likely to be varied depending on the cycle of amplification termination and the cycle for melting analysis.

U.S. Pat. No. 8,039,215 discloses that a melting analysis in target amplification is performed to obtain the maximum values of melting peaks for each amplification cycle and a cycle reaching to the maximum value over a threshold value is determined, thereby quantifying a target sequence. Because this method requires melting analyses for most of amplification cycles to determine a cycle reaching to the maximum value over a threshold value, it demands longer analysis time.

Under such circumstances of conventional technologies, the present inventor has recognized that a plurality of target sequences can be simultaneously detected and quantified in a more effective manner, when a quantification method using a melting analysis for detection of a plurality of target sequences with a single detecting channel and being capable for providing improved quantification results in more rapid manner is developed.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventor has made intensive researches to develop methods for quantifying a target nucleic acid sequence in a more convenient and effective manner. As a result, the present inventor has established a novel protocol in which amplified products obtained at at least two predetermined amplification cycles is directly or indirectly used for a melting analysis, thereby quantifying the target nucleic acid sequence. The present invention for quantifying the target nucleic acid sequence can overcome problems associated with conventional quantifying methods.

Accordingly, the object of this invention is to provide a method for quantifying a target nucleic acid sequence in a nucleic acid sample using a melting peak curve.

Other objects and advantages of the present invention will become apparent from the detailed description to follow taken in conjugation with the appended claims.

DETAILED DESCRIPTION OF THIS INVENTION

In an aspect of this invention, there is provided a method for quantifying a target nucleic acid sequence in a nucleic acid sample using a melting peak curve:

(a) amplifying the target nucleic acid sequence in the nucleic acid sample to form a duplex comprising a labeling moiety by cycles of repeating a series of reactions; wherein the duplex comprises the amplified target nucleic acid sequence in a double strand, a duplex formed by hybridization between the target nucleic acid sequence and a probe, or a duplex formed dependent on the existence of the target nucleic acid sequence; wherein the formation of duplex increases in proportion to the amplification of the target nucleic acid sequence; wherein the labeling moiety generates a detectable signal during association or dissociation of the duplex;

(b) obtaining a melting peak curve for at least two predetermined cycles during the repetition in the step (a) by performing a melting analysis at the predetermined cycles over a range of temperatures in which the detectable signal from the duplex is detected; and (c) quantifying the target nucleic acid sequence using the melting peak curve.

The present inventor has made intensive researches to develop methods for quantifying a target nucleic acid sequence in a more convenient and effective manner. As a result, the present inventor has established a novel protocol in which amplified products obtained at at least two predetermined amplification cycles is directly or indirectly used for a melting analysis, thereby quantifying the target nucleic acid sequence. The present invention for quantifying the target nucleic acid sequence can overcome problems associated with conventional quantifying methods.

The present invention will be described in more detail as follows:

Step (a): Formation of a Duplex Comprising a Labeling Moiety

According to the present invention, a target nucleic acid sequence is amplified to form a duplex comprising a labeling moiety.

The term used herein "target nucleic acid", "target nucleic acid sequence" or "target sequence" refers to a nucleic acid sequence of interest for quantification. The target nucleic acid sequence comprises a sequence in a single strand as well as in a double strand. The target nucleic acid sequence comprises a sequence initially present in a nucleic acid sample as well as a sequence newly generated in reactions.

According to an embodiment, the target nucleic acid sequence is annealed to or hybridized with a primer or probe under certain amplification and hybridization conditions.

According to an embodiment, the target nucleic acid sequence is amplified by cycles of repeating a series of reactions.

According to an embodiment, the amplification of the target nucleic acid sequence is performed by PCR (polymerase chain reaction), LCR (ligase chain reaction, see Wiedmann M, et al., "Ligase chain reaction (LCR)—overview and applications." PCR Methods and Applications 1994 February; 3(4):S51-64), Barany F. "Genetic disease detection and DNA amplification using cloned thermostable ligase." Proc Natl Acad Sci USA., 88(1):189-93 (1991)), GLCR (gap filling LCR, see WO 90/01069, EP 439182 WO 93/00447), Q-beta (Q-beta replicase amplification, see Cahill P, et al., "Polymerase chain reaction and Q beta replicase amplification" Clin Chem., 37(9):1482-5 (1991), U.S. Pat. No. 5,556,751), SDA (strand displacement amplification, see G T Walker et al., "Strand displacement amplification—an isothermal, in vitro DNA amplification technique" Nucleic Acids Res. 20(7):16911696 (1992), EP 497272), 3SR (self-sustained sequence replication, see Mueller J D et al., "Self-sustained sequence replication (3SR): an alternative to PCR" Histochem Cell Biol. 108(4-5):431-7 (1997), NASBA (nucleic acid sequence-based amplification, see Compton, J. "Nucleic acid sequence-based amplification". Nature 350(6313):912 (1991); Keightley, M C et al., "Real-time NASBA detection of SARS-associated coronavirus and comparison with real-time reverse transcription-PCR". Journal of medical virology 77(4):6028 (2005)), TMA (Transcription-Mediated Amplification, see Hofmann W P et al., "Comparison of transcription mediated amplification (TMA) and reverse transcription polymerase chain reaction (RT-PCR) for detection of hepatitis C virus RNA in liver tissue" J Clin Virol. 32(4):289-93 (2005); U.S. Pat. No. 5,888,779).) or RCA (Rolling Circle Amplification, see Hutchison C. A. et al., "Cell-free cloning using phi29 DNA polymerase" Proc. Natl Acad. Sci. USA. 102:1733217336 (2005); Dean F. B., et al., Nelson J. R. et al., "Rapid amplification of plasmid and phage DNA using Phi 29 DNA polymerase and multiply-primed rolling circle amplification. Genome Res. 11:10951099(2001)).

The amplification methods described above may amplify through repeating a series of reactions with or without changing temperatures. The unit of amplification comprising the repetition of a series of reactions is expressed as a "cycle". The unit of cycles may be expressed as the number of the repetition or time being dependent on amplification methods.

The term used herein "cycle" may have a unit as one (1) repetition of a series of reactions or a unit as repetitions of a series of reactions performed in a time interval.

According to an embodiment, the amplification of the target nucleic acid sequence is accomplished under conditions of changed temperatures by the repetition of the series of reactions comprising hybridization between a primer for amplification and the target nucleic acid sequence, extension of the primer and dissociation of an extended strand, and the cycle has a unit as one (1) repetition of the series of reactions. One (1) repetition of the series of reactions is expressed as one cycle and two repetitions as two cycles.

According to an embodiment, the amplification of the target nucleic acid sequence is accomplished under isothermal conditions by the repetition of the series of reactions, and the cycle has a unit as repetitions of a series of reactions performed in a time interval. For example, where the unit of the cycle is defined as repetitions of a series of reactions performed in one (1) minute, the repetitions of a series of reactions performed in one (1) minute are expressed as one-minute cycle (or one cycle) and the repetitions of a series of reactions performed in two minutes as two-minute cycles (two cycles).

According to an embodiment, the amplification of the target nucleic acid sequence is performed by PCR. PCR is widely used in the art to amplify nucleic acid molecules and comprises repetition cycles of denaturation of target sequences, annealing (hybridization) to target sequences and primer extension (U.S. Pat. Nos. 4,683,195, 4,683,202, and 4,800,159; Saiki et al., (1985) Science 230, 1350-1354).

The target nucleic acid sequence to be amplified may include any DNA (gDNA and cDNA), RNA molecules their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al., *Nucleic Acids Res.* 16:10366 (1988)). For reverse transcription, an oligonucleotide dT primer hybridizable to poly A tail of mRNA, random primers or target-specific primers may be used.

The present methods do not require that the template nucleic acid molecules have any particular sequence or length. In particular, the molecules include any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature.

A primer is hybridized or annealed to a region on the target sequence (template) so that double-stranded structure is formed.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

According to an embodiment, the primer used for the present invention has a dual priming (DPO) structure developed by the present inventor. The oligonucleotide having the DPO structure exhibits much higher target specificity than conventional primers and probes (see WO 2006/095981; Chun et al., Dual priming oligonucleotide system for the multiplex detection of respiratory viruses and SNP genotyping of CYP2C19 gene, *Nucleic Acid Research*, 35:6e40 (2007)).

The term used herein "probe" refers to a single-stranded nucleic acid molecule comprising a portion or portions that are substantially complementary to a target nucleic acid sequence.

According to an embodiment, the primer and probe is an oligodeoxyribonucleotide in a single strand. the primer and probe can be comprised of naturally occurring dNMP (i.e., dAMP, dGM, dCMP and dTMP), modified nucleotide or non-natural nucleotide. For example, the primer and probe may comprise PNA (Peptide Nucleic Acid, see WO 92/20702) or LNA (Locked Nucleic Acid, see WO 98/22489, WO 98/39352 and WO 99/14226). The primer and probe can also include ribonucleotides.

The term "annealing" or "hybridization" as used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The annealing of the primer for amplification to the target sequence may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (primers) and the target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The primers used in the present invention have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary". In an embodiment, the term "complementary" means "perfectly complementary".

The primer annealed to the target sequence is extended by a template-dependent polymerase, including "Klenow" fragment of *E. coli* DNA polymerase I, a thermostable DNA polymerase, and bacteriophage T7 DNA polymerase. In an embodiment, the template-dependent polymerase is a thermostable DNA polymerase obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophllus*, *Thermus chliarophllus*, *Thermus flavus*, *Thermus igniterrae*, *Thermus lacteus*, *Thermus oshimai*; *Thermus ruber*, *Thermus rubens*, *Thermus scotoductus*, *Thermus silvans*, *Thermus* species Z05, *Thermus* species sps 17, *Thermus thermophilus*, *Thermotoga maritima*, *Thermotoga neapolitana*, *Thermosipho africanus*, *Thermococcus Thermococcus barossi*, *Thermococcus gorgonarius*, *Thermotoga maritima*, *Thermotoga neapolitana*, *Thermosiphoafricanus*, *Pyrococcus woesei*, *Pyrococcus horikoshii*, *Pyrococcus abyssi*, *Pyrodictium occultum*, *Aquifex pyrophllus* and *Aquifex aeolieus*.

When a polymerization reaction is being conducted, the components required for such reaction may be provided in excess in the reaction vessel. Excess in reference to components of the extension reaction refers to an amount of each component such that the ability to achieve the desired extension is not substantially limited by the concentration of that component. It is desirable to provide to the reaction mixture an amount of required cofactors such as $Mg^{2+}$, dATP, dCTP, dGTP, and dTTP in sufficient quantity to support the degree of the extension desired.

The duplex capable of providing a detection signal is formed by the amplification reaction.

The term "detection signal" means any signal indicating the formation of the duplex which demonstrate the presence of the target nucleic acid sequence. The duplex demonstrates the presence of the target nucleic acid sequence, which is determined by detecting the detection signal.

According to an embodiment, the duplex used in the present invention is an amplicon in a double strand formed by the amplification reaction, a duplex formed by hybridization between the target nucleic acid sequence and a probe, or a duplex formed dependent on the existence of the target nucleic acid sequence.

According to an embodiment, for the duplex formed by hybridization between the target nucleic acid sequence and a probe, the probe is a probe hybridizable with an internal sequence of the amplicon in a double strand formed by the amplification reaction. The probe includes any probe capable of providing a signal in the melting analysis, for example, Molecular Beacon™ (U.S. Pat. No. 5,925,517), Hybeacons™ (D. J. French, et al., Molecular and Cellular Probes (2001) 13, 363374 and U.S. Pat. No. 7,348,141), Dual-labeled, self-quenched probe (U.S. Pat. No. 5,876, 930), LUX™ (I. A. Nazarenko, et al. Nucleic Acids Res 2002, 30:2089-2095. and U.S. Pat. No. 7,537,886), Hybridization probe (Bernard P S, et al., Clin Chem 2000, 46, 147-148 and U.S. Pat. No. 6,174,670).

The duplex formed dependent on the existence of the target nucleic acid sequence is not an amplicon of the target sequence per se formed by the amplification reaction but a duplex whose amount is increased in proportion to the amplification of the target nucleic acid sequence. The duplex formed dependent on the existence of the target nucleic acid sequence may be obtained in accordance with various methods.

According to an embodiment, the duplex formed dependent on the existence of the target nucleic acid sequence may be obtained by a PTOCE (PTO Cleavage and Extension) method developed by the present inventor (see WO 2012/096523), teachings of which are incorporated herein by reference.

Briefly, the PTOCE comprises the steps of: (a) hybridizing the target nucleic acid sequence with an upstream oligonucleotide and a PTO (Probing and Tagging Oligonucleotide); wherein the upstream oligonucleotide comprises a hybridizing nucleotide sequence complementary to the target nucleic acid sequence; wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the upstream oligonucleotide is located upstream of the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with a CTO (Capturing and Templating Oligonucleotide); wherein the CTO comprises in a 3' to 5' direction (i) a capturing portion comprising a nucleotide sequence complementary to the 5'-tagging portion or a part of the 5'-tagging portion of the PTO and (ii) a templating portion comprising a nucleotide sequence non-complementary to the 5'-tagging portion and the 3'-targeting portion of the PTO; wherein the fragment released from the PTO is hybridized with the capturing portion of the CTO; and (d) performing an extension reaction using the resultant of the step (c) and a template-dependent nucleic acid polymerase; wherein the fragment hybridized with the capturing portion of the CTO is extended and a extended duplex is formed; wherein the extended duplex has a $T_m$ value adjustable by (i) a sequence and/or length of the fragment, (ii) a sequence and/or length of the CTO or (iii) the sequence and/or length of the fragment and the sequence and/or length of the CTO.

The extended duplex formed in the step (d) of the PTOCE is an example of the duplex used in the present invention.

Where the PTOCE method is applied to the present invention, the present invention comprises the following steps: (a) amplifying the target nucleic acid sequences using the PTO, the primer and a template-dependent nucleic acid polymerase having a 5' nuclease activity, and cleaving the PTO to release a fragment; and (b) hybridizing the fragment released from the PTO with a CTO and then forming an extended duplex using a template-dependent nucleic acid polymerase.

The 5'-tagging portion of the PTO comprises a nucleotide sequence non-complementary to the target nucleic acid sequence. The templating portion of the CTO comprises a nucleotide sequence non-complementary to the 5'-tagging portion and the 3'-targeting portion of the PTO.

The term used herein "PTO (Probing and Tagging Oligonucleotide)" means an oligonucleotide comprising (i) a 3'-targeting portion serving as a probe and (ii) a 5'-tagging portion with a nucleotide sequence non-complementary to the target nucleic acid sequence, which is nucleolytically released from the PTO after hybridization with the target nucleic acid sequence. The 5'-tagging portion and the 3'-targeting portion in the PTO have to be positioned in a 5' to 3' order.

The PTO does not require any specific lengths. For example, the length of the PTO may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO may be in any lengths so long as it is specifically hybridized with target nucleic acid sequences. For example, the 3'-targeting portion of the PTO may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the templating portion of the CTO and then extended. For instance, the 5'-tagging portion of the PTO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO may have a 3'-OH terminal. In an embodiment, the 3'-end of the PTO is "blocked" to prohibit its extension.

The CTO is acted as a template for extension of the fragment released from the PTO. The fragment serving as a primer is hybridized with the CTO and extended to form an extended duplex.

The templating portion may comprise any sequence so long as it is non-complementary to the 5'-tagging portion and the 3'-targeting portion of the PTO. Furthermore, the templating portion may comprise any sequence so long as it can be acted as a template for extension of the fragment released from the PTO.

As described above, when the fragment having the 5'-tagging portion of the PTO is released, it is preferred that the capturing portion of the CTO is designed to comprise a nucleotide sequence complementary to the 5'-tagging portion. When the fragment having the 5'-tagging portion and a 5'-end part of the 3'-targeting portion is released, it is preferred that the capturing portion of the CTO is designed to comprise a nucleotide sequence complementary to the 5'-tagging portion and the 5'-end part of the 3'-targeting portion. When the fragment having a part of the 5'-tagging portion of the PTO is released, it is preferred that the capturing portion of the CTO is designed to comprise a nucleotide sequence complementary to the part of the 5'-tagging portion.

Moreover, it is possible to design the capturing portion of the CTO with anticipating cleavage sites of the PTO. For example, where the capturing portion of the CTO is designed to comprise a nucleotide sequence complementary to the 5'-tagging portion, either the fragment having a part of the 5'-tagging portion or the fragment having the 5'-tagging portion can be hybridized with the capturing portion and then extended. Where the fragment comprising the 5'-tagging portion and a 5'-end part of the 3'-targeting portion is released, it may be hybridized with the capturing portion of the CTO designed to comprise a nucleotide sequence complementary to the 5'-tagging portion and then successfully extended although mismatch nucleotides are present at the 3'-end portion of the fragment. That is because primers can be extended depending on reaction conditions although its 3'-end contains some mismatch nucleotides (e.g. 1-3 mismatch nucleotides).

When the fragment comprising the 5'-tagging portion and a 5'-end part of the 3'-targeting portion is released, the 5'-end part of the capturing portion of the CTO may be designed to have a nucleotide sequence complementary to the cleaved 5'-end part of the 3'-targeting portion, overcoming problems associated with mismatch nucleotides.

The length of the CTO may be widely varied. For example, the CTO is 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO. For example, the templating portion of the CTO is 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. In an embodiment, the 3'-end of the CTO is blocked to prohibit its extension.

The duplex formed by the PTOCE method is an example of the duplex formed dependent on the existence of the target nucleic acid sequence.

Another example of the duplex formed dependent on the existence of the target nucleic acid sequence includes a duplex between a strand of the duplex formed by the PTOCE method and a probe specifically hybridized with the strand.

The duplex for the melting analysis may be formed in a target-dependent manner by other methods and used for the quantification method of the present invention.

The labeling moiety (label) generates a detectable signal during association or dissociation of the duplex.

According to an embodiment, the label may be linked to a double stranded amplicon formed in the amplification reaction. The amplification primer may comprise the label. In another embodiment using the duplex between the target nucleic acid sequence and a probe, the label is linked to the probe or both the target nucleic acid sequence and the probe. In an embodiment using the duplex formed dependent on the existence of the target nucleic acid sequence, oligonucleotides for formation of the duplex may comprise the label. For example, when the PTOCE method is employed, the label may be linked to the fragment released from the PTO and/or CTO.

According to an embodiment, the labeling moiety of the duplex is a single label linked to a single strand of the duplex, an interactive dual label containing a reporter molecule and a quencher molecule all of which are linked to a strand of the duplex (intrastrand interactive dual label), an interactive dual label containing a reporter molecule and a quencher molecule one of which is linked to one strand of the duplex and the other is linked to the other strand of the duplex (interstrand interactive dual label) or an intercalating dye to be intercalated in the duplex.

The single label includes, for example, a fluorescent label, a luminescent label, a chemiluminescent label, an electrochemical label and a metal label.

According to an embodiment, the single label provides a different signal (e.g., different signal intensities) depending on its presence on a double strand or single strand.

According to an embodiment, the single label is a fluorescent label. The preferable types and binding sites of single fluorescent labels used in this invention are disclosed U.S. Pat. Nos. 7,537,886 and 7,348,141, the teachings of which are incorporated herein by reference in their entity. For example, the single fluorescent label includes JOE, FAM, TAMRA, ROX and fluorescein-based label.

The single label may be linked to oligonucleotides by various methods. For instance, the label is linked to probes through a spacer containing carbon atoms (e.g., 3-carbon spacer, 6-carbon spacer or 12-carbon spacer).

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The interactive label system includes a dual label based on "on contact-mediated quenching" (Salvatore et al., Nucleic Acids Research, 2002 (30) no. 21 e122 and Johansson et al., J. AM. CHEM. SOC 2002 (124) pp 6950-6956). The interactive label system includes any label system in which signal change is induced by interaction between at least two molecules (e.g. dye).

The reporter molecule and the quencher molecule useful in the present invention may include any molecules known in the art. Examples of those are: Cy2™ (506), YO-PRO™-1 (509); YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DiIC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable fluorescence molecule and suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent quencher molecule (e.g. black quencher or dark quencher) capable of quenching a fluorescence of a wide range of wavelengths or a specific wavelength may be used in the present invention. Examples of those are BHQ and DABCYL.

In the signaling system comprising the reporter and quencher molecules, the reporter encompasses a donor of FRET and the quencher encompasses the other partner (acceptor) of FRET. For example, a fluorescein dye is used as the reporter and a rhodamine dye as the quencher.

Exemplified intercalating dyes useful in this invention include SYBR™ Green I, PO-PRO™-1, BO-PRO™-1, SYTO™43, SYTO™44, SYTO™45, SYTOX™ Blue, POPOTm-1, POPO™-3, BOBO™-1, BOBO™-3, LO-PRO™-1, JO-PRO™-1, YO-PRO™1, TO-PRO™1, SYTO™ 11, SYTO™13, SYTO™15, SYTO™16, SYTO™20, SYTO™23, TOTO™-3, YOYO™3, GelStar™ and thiazole orange. The intercalating dyes intercalate specifically into double-stranded nucleic acid molecules to generate signals.

The label and signal generation in the PTOCE method applicable to the present invention are described in WO 2012/096523. Where the PTOCE method is applied to the present invention, the label and signal generation are exemplified as follows:

Where an interactive dual label containing a reporter molecule and a quencher molecule all of which are linked to a strand of the duplex (i.e., intrastrand dual label) is used, the fragment released from the PTO or the CTO comprises an interactive dual label comprising a reporter molecule and a quencher molecule; the melting of the duplex in the step (b) induces to provide signal from the interactive dual label. In an embodiment, the reporter molecule and the quencher molecule are linked to the 5'-end and the 3'-end of the CTO. For example, one of the reporter molecule and the quencher molecule on the CTO is located at its 5'-end or at 0-5 nucleotides apart from its 5'-end and the other is located to quench or unquench the signal from the reporter molecule depending on conformation of CTO. As another example, one of the reporter molecule and the quencher molecule on the CTO is located at its 3'-end or at 0-5 nucleotides apart from its 3'-end and the other is located to quench or unquench the signal from the reporter molecule depending on conformation of CTO.

Where an interactive dual label containing a reporter molecule and a quencher molecule each of which is linked to each of a two strand of the duplex (i.e., interstrand dual label) is used, the PTO fragment has one of an interactive dual label comprising a reporter molecule and a quencher molecule and the CTO has the other of the interactive dual label and the melting of the duplex in the step (b) induces to provide signal from the interactive dual label. The reporter molecule and the quencher molecule may be located at any site of the PTO fragment and the CTO, so long as the signal from the reporter molecule is quenched by the quencher molecule in the duplex. For example, the reporter molecule or the quencher molecule on the PTO fragment is located at the 5'-end of the 5'-tagging portion. For example, the reporter molecule or the quencher molecule on the CTO is located at its 3'-end.

Where a single label linked to a single strand of the duplex is used, the PTO fragment or the CTO has the single label and the melting of the duplex in the step (b) induces to provide signal from the single label. The single label may be located at any site on the CTO, so long as the signal level from the single label is changed depending on melting of the duplex. For example, the single label is linked to the templating portion or to the capturing portion of the CTO. The single label may be located at any site on the PTO fragment, so long as the signal level from the single label is changed depending on melting of the duplex.

Step (b): Melting of the Duplex and Melting Peak Curve

Afterwards, during the amplification of the target nucleic acid sequence, the signal from the duplex is detected at at least two predetermined cycles over a range of temperatures (melting analysis). The signal detection includes the detection of signal generated by melting the duplex formed in the step (a) over a range of temperatures and the detection of signal generated by melting the duplex formed in the step (a) and then hybridizing over a range of temperatures.

The feature of the present invention is to perform a melting analysis for each amplicon (or duplex indicating the amplicon) obtained from at least two predetermined cycles during the amplification of the target nucleic acid sequence.

Conventional melting analyses or melting peak analyses are performed at once after completion of target amplification. Alternatively, another conventional method is to perform a melting analysis for most of cycles during target amplification in order to find a cycle showing a melting peak height of a predetermined threshold value (see U.S. Pat. No. 8,039,215).

Unlike to the conventional methods, the present invention is performed in such a manner that a melting analysis is carried out for amplicons (or duplexes indicating the amplicons) obtained from at least two predetermined cycles during the amplification of the target nucleic acid sequence and then the results of the melting analysis are utilized for quantification, thereby completely overcoming problems of conventional methods in light of accuracy, rapidness and convenience of quantification analysis.

The step (b) may be carried out by various melting analysis processes known to one of skill in the art. The term "melting analysis" used herein is intended to encompass not only a melting analysis in a narrow sense but also a hybridization analysis, unless otherwise indicated. The melting analysis in a narrow sense refers to a method in which the dissociation of duplexes is measured under increasing stringency conditions by adjusting temperatures. The hybridization analysis in a narrow sense refers to a method in which the association of duplexes is measured under decreasing stringency conditions by adjusting temperatures.

The term "melting curve" or "melting peak curve" used herein is intended to encompass not only a melting curve or melting peak curve from a melting analysis in a narrow sense but also a hybridization curve or hybridization peak curve from a hybridization analysis, unless otherwise indicated.

The melting curve or hybridization curve may be obtained by conventional technologies, for example, as described in U.S. Pat. Nos. 6,174,670 and 5,789,167, Drobyshev et al, Gene 188: 45 (1997); Kochinsky and Mirzabekov Human Mutation 19:343 (2002); Livehits et al J. Biomol. Structure Dynam. 11:783 (1994); and Howell et al Nature Biotechnology 17:87 (1999). For example, a melting curve or hybridization curve may consist of a graphic plot or display of the variation of the output signal with the parameter of hybridization stringency. Output signal may be plotted directly against the hybridization parameter. Typically, a melting curve or hybridization curve will have the output signal, for example fluorescence, which indicates the degree of duplex structure (i.e. the extent of hybridization), plotted on the Y-axis and the hybridization parameter on the X axis.

The melting (hybridization) curve analysis and the melting (hybridization) peak analysis will be described with reference to disclosures of U.S. Pat. No. 8,039,215.

Before the performance of the present method, at least two cycles are predetermined for a melting curve analysis and then the melting curve analysis is carried out at the predetermined cycles during the target amplification.

The melting curve analysis may be performed before, during or after the predetermined cycles.

The cycle subject to the melting curve analysis may be predetermined in considering features of amplification methods. For example, where the PCR amplification method is employed, the cycles for the melting curve analysis may be selected in considering an initial step of amplification, exponential amplification step and saturation step of amplification. Usually, the cycle and number for the melting curve analysis may be selected in considering the amount range of target nucleic acid sequences in samples.

According to an embodiment, the number of cycles for the melting curve analysis is at least 2, 3, 4, 5 or 6, and at most 40, 30, 20, 15, 10 or 8.

In a particular embodiment, the number of cycles for the melting curve analysis is 2-40, 2-30, 2-20, 2-15, 2-10, 2-7, 2-5, 3-40, 3-30, 3-20, 3-15, 3-10, 3-7 or 3-5.

According to an embodiment, the interval between cycles for the melting curve analysis is at least 2, 5, 10, 15, or 20 cycles and at most 40, 30 or 20 cycles.

In a particular embodiment, the interval between cycles for the melting curve analysis is 2-40, 5-20, 5-15 or 10-15 cycles.

For example, if $20^{th}$, $30^{th}$ and $40^{th}$ are chosen for melting analysis, the number of cycle for melting curve analysis is 3 and the interval between cycles is 10 cycles in this case.

Step (c): Quantification Analysis Using Melting Peak Curve

The quantification of the target nucleic acid sequence is then performed using the melting peak curve.

The feature of the present invention is to calculate a value for quantifying from the melting peak curve and then to quantify the target nucleic acid sequence by use of the value for quantifying.

According to an embodiment, the target nucleic acid sequence is quantified using the presence or absence of the melting peak curve at the predetermined cycle.

According to another embodiment, the target nucleic acid sequence is quantified using the height or area of the melting peak curve at the predetermined cycle.

The melting curves are obtained through the detection of signals from at least two predetermined cycles and then the melting peaks are obtained. Afterwards, the maximum height values or area values of the melting peak curves are obtained. As the amount of the target nucleic acid sequence is greater, the melting peak curve is obtained at an earlier cycle, which is used for the quantification of the target nucleic acid sequence. The maximum height values or area values of the melting peak curves can reflect the amount of the duplex which generates signal. The amount of the duplex is in proportion to the amount of the target nucleic acid sequence. Therefore, the maximum height values or area values of the melting peak curves can reflect the initial amount of the target nucleic acid sequence.

The quantification of the target nucleic acid sequence may be carried out by use of the presence (or absence) of melting peaks obtained at the at least two predetermined amplification cycles, and/or the height or area of the melting peaks in various manners.

The height or area of the melting peaks provided by melting peak curves may be used for quantification of the target nucleic acid sequence without derivations (or modification) or with derivations (or modification) in a particular rule.

Where values of melting peak curves (e.g., height and area) are used together with the reference values assigned to the predetermined cycles showing the melting peak curve, the reference values may be pre-selected in considering the magnitude of values of melting peak curves.

According to an embodiment, the height and area of the melting peaks is the maximum height and area.

In the first approach, the initial amount of the target nucleic acid sequence is quantified using all melting peak curve obtained at the at least two predetermined cycles.

According to an embodiment, a calculation (e.g. add, subtract, multiply or divide) is carried out by use of all the reference values of the predetermined cycles to show the melting peak curve and/or all the values of melting peak curves (e.g., height and area) in order to obtain a value for quantifying, and then the initial amount of the target nucleic acid sequence is determined.

According to an embodiment, a calculation (e.g. add, subtract, multiply or divide) is carried out by use of all the reference values of the predetermined cycles to show the melting peak curve and/or some of the values of melting peak curves (e.g., height and area) in order to obtain a value for quantifying, and then the initial amount of the target nucleic acid sequence is determined.

According to an embodiment, a calculation (e.g. add, subtract, multiply or divide) is carried out by use of some of the reference values of the predetermined cycles to show the melting peak curve and/or all of the values of melting peak curves (e.g., height and area) in order to obtain a value for quantifying, and then the initial amount of the target nucleic acid sequence is determined.

According to a particular embodiment, the all of maximum height values or area values of the melting peak curves obtained at the predetermined cycles are added to quantify an initial amount of the target nucleic acid sequence. For example, three cycles (30, 40 and 50 cycles) subject to the melting analysis are pre-selected, the amplification reaction is then underwent and the melting analysis is preformed to obtain melting peaks. The maximum height values or area values of the melting peak curves are added and the added values are compared for quantification. For example, as the added values are greater, the initial amount of the target nucleic acid sequence is determined to be greater.

According to another particular embodiment, the reference values are assigned to the at least two predetermined cycles and the reference values assigned to the at least two predetermined cycles to show the melting peak curves are added to quantify an initial amount of the target nucleic acid sequence. For example, three cycles (30, 40 and 50 cycles) subject to the melting analysis are predetermined and the reference values, 30, 40 and 50 are assigned to the predetermined cycles, respectively. Where melting peak curves are observed at 40 and 50 cycles, the reference values 40 and 50 are added and the addition value "90" are used to quantify an initial amount of the target nucleic acid sequence. The same value of the reference values (e.g., 100, 100, 100) may be assigned to each of the predetermined cycles. Alternatively, the reference values in ascending (e.g., 100, 200, 300) or descending order (e.g., 300, 200, 100) may be assigned to the predetermined cycles. The reference values should be assigned in considering the followings: For example, the addition value of the reference values assigned to 30, 40 and 50 cycles is higher than the addition value of the reference values assigned to 40 and 50 cycles that is higher than the addition value of the reference value assigned to 50 cycles.

According to an embodiment, in determining whether the predetermined cycles show a melting peak curve, it would be determined that a melting peak curve for quantification is shown (i.e., determination with threshold values) in the case that the maximum height value or the maximum area of the melting peak curves value is higher than a predetermined value (i.e., threshold values).

According to another particular embodiment, supplementary values are added in considering the maximum height value or the maximum area value of a firstly-observed melting peak. This particular embodiment may be employed to evaluate difference in the amounts in samples showing a firstly-observed melting peak at the same cycle. As a method for calculating supplementary values by considering the maximum height value or the maximum area value of a firstly-observed melting peak, the relative ratio of the maximum height value or the maximum area value of melting peaks practically obtained to the maximum height value or the maximum area value of melting peaks obtained at saturation stage of target amplification is used.

In the second approach, the initial amount of the target nucleic acid sequence is quantified using a first melting peak curve among melting peak curves obtained at the at least two predetermined cycles.

According to an embodiment, values for quantifying are obtained using the reference value of the predetermined cycle to show a first melting peak curve and/or values of the first melting peak curves (e.g., height and area) and then the initial amount of the target nucleic acid sequence is quantified using the values for quantifying. For obtaining the values for quantifying, a calculation (add, subtract, multiply or divide) may be carried out.

According to a particular embodiment, the step (c) is performed by assigning a reference value to each of the at least two predetermined cycles and calculating a value for quantifying by use of the reference value of the predetermined cycle to show a first melting peak curve, such that an initial amount of the target nucleic acid sequence is quantified. For example, the reference values per se are used as the values for quantifying.

According to another particular embodiment, the step (c) is performed by assigning a reference value to each of the at least two predetermined cycles and calculating a value for quantifying by use of (i) the reference value of the predetermined cycle to show a first melting peak curve and (ii) a maximum height values or area value of the first melting peak curve, such that an initial amount of the target nucleic acid sequence is quantified.

According to more particular embodiment, the step (c) is performed by assigning a reference value to each of the at least two predetermined cycles and calculating a value for quantifying by modifying (derivatizing) the reference value of the predetermined cycle to show a first melting peak curve with a maximum height value or area value of the first melting peak curve, such that an initial amount of the target nucleic acid sequence is quantified. For example, the modification (derivatization) of the reference value is addition of the reference value and the maximum height value (or maximum area value) of the first melting peak curve. Alternatively, the modification (derivatization) is application of maximum height value (or maximum area value) of the first melting peak curve to the reference value in accordance with a particular rule (e.g., proportional application). As a method for applying the maximum height value (or maximum area value) of the first melting peak curve to the reference value, the relative ratio of the maximum height value or the maximum area value of melting peaks practically obtained to the maximum height value or the maximum area value of melting peaks obtained at saturation stage of target amplification is used.

For example, three cycles (20, 30 and 40 cycles) subject to the melting analysis are predetermined and the reference values, 100, 1 and 0.01 are assigned to the predetermined cycles, respectively. The relative ratio of the maximum height value of melting peaks practically obtained at the three cycles to the maximum height value of melting peaks obtained at saturation stage of target amplification is then calculated. For instance, where the maximum height value of melting peaks practically obtained is 120, and the maximum height value of melting peaks obtained at saturation stage of target amplification is 500, the relative ratio is 0.24 (120/500). The relative ratio to be calculated may be obtained by rounding up the second decimal number or using certain range value. For example, where a range is quartered as 0.25, 0.5, 0.75 and 1 and an observed value is 0.24, the observed value is treated as 0.25.

Assuming that a first melting peak curve with the maximum height value ratio of 0.2 is observed at 20 cycle in Sample A and a first melting peak curve with the maximum height value ratio of 0.3 is observed at 20 cycle in Sample B, the value for quantifying for Sample A is 20 (100×0.2) and the value for quantifying for Sample B is 30 (100×0.3). Therefore, it can be evaluated that Sample B contains the initial amount of a target nucleic acid sequence higher than Sample A. Assuming that a first melting peak curve with the maximum height value ratio of 0.3 is observed at 30 cycle in Sample C, the value for quantifying for Sample C is 0.3 (1×0.3). Therefore, it can be evaluated that Sample C contains the initial amount of a target nucleic acid sequence lower than Sample A and B. This example corresponds, to a relative quantification.

According to an embodiment, in the second approach, the reference value and the calculation method of the value for quantifying are determined such that a minimum value of the value for quantifying to be calculated from a predetermined cycle to show the first melting peak curve is higher than or the same as a maximum value for a value for quantifying to be calculated when a first melting peak curve is observed at a cycle following the predetermined cycle.

Alternatively, the reference values in ascending order (e.g., 0.01, 1, 100) may be assigned to the predetermined cycles and a lower ratio values is obtained as maximum value of melting peak is greater.

For example, the calculation of the ratio may be done by dividing the maximum height value of melting peaks obtained at saturation stage of target amplification by the maximum height value of melting peaks practically obtained at the predetermined cycle. Where the value for quantifying is calculated to be lower, it can be evaluated that the initial amount of the target nucleic acid sequence is higher. For such calculation, the reference value and the calculation of the value for quantifying are determined such that a maximum value of the value for quantifying to be calculated from a predetermined cycle to show the first melting peak curve is lower than or the same as a minimum value for a value for quantifying to be calculated when a first melting peak curve is observed at a cycle following the predetermined cycle.

The numerical values described above are only examples. The predetermined cycles, interval of reference values, assignment of particular values, modification (derivatization) method of maximum height or area values of melting peak for calculating a value for quantifying, calculation of reference values, and introduction of maximum height or area values of melting peak or their modification values into values for quantifying may be performed in various manners.

The approaches for embodying the present invention described above may be performed in an individual or combinatorial manner. Alternatively, other approaches may be performed in such a manner that melting peaks are obtained by melting analysis in a predetermined range of cycles and then an initial amount of a target nucleic acid sequence is quantified using the melting peaks in various processes.

According to an embodiment, the relative or absolute quantification of the target nucleic acid sequence is performed by comparing a value for quantifying obtained by applying another nucleic acid sample or a control sample with a known nucleic acid concentration to the steps (a)-(c). Where the control sample has narrower concentration interval (e.g., 1 pg, 10 pg, 20 pg, 30 pg and so on) and the values for quantification for the control sample are then obtained, the absolute quantification of the target nucleic acid sequence may be done in more accurate manner.

According to an embodiment, the quantification of the target nucleic acid sequence provides certain numerical results (e.g., 100 pg).

According to an embodiment, the quantification of the target nucleic acid sequence provides a range of values (e.g., less than 1000 pg and more than 10 pg, or 10-1000 pg)

The quantification of another nucleic acid sample or the control sample may be performed in the same vessel as or different vessel from a reaction vessel for the target nucleic acid sequence.

The advantages of the present invention may be highlighted in the simultaneous (multiplex) quantification of at least two target nucleic acid sequences.

According to an embodiment, the duplexes produced from the target nucleic acids have different Tm values, respectively.

According to an embodiment, the target nucleic acid sequence comprises at least two target nucleic acid sequences. Where the quantification of at least two target nucleic acid sequences is performed in a reaction vessel, each target nucleic acid sequence may be absolutely quantified and the target nucleic acid sequences may be quantified relatively to each other.

The present invention is also useful in quantification of a nucleic acid sequence containing a nucleotide variation. According to an embodiment, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and its any mutant type at a particular location in a nucleic acid sequence.

The present invention may be performed both in a liquid phase and on a solid phase.

The features and advantages of this invention will be summarized as follows:

(a) The present invention is performed in such a manner that at least two cycles in the nucleic acid amplification subject to melting peak analysis are predetermined before the nucleic acid amplification and melting peak analyses are performed for the predetermined at least two cycles, followed by quantifying the target nucleic acid sequence using data values from the melting peak curve (e.g., the presence or absence, height and area).

Among conventional technologies, a quantification method by performing melting analysis at once after target amplification has serious problems in that the quantification results may be varied depending on the cycles of target amplification. Because the present invention performs a melting peak analysis at the at least two predetermined cycles during target amplification, it is able to provide more accurate and significant quantification results than the conventional method.

In the methods disclosed in U.S. Pat. No. 8,039,215, a melting analysis has to be conducted at each cycle of target amplification so as to verify a cycle showing a threshold melting peak maximum value, which leads to much longer analysis time. Because the present invention performs a melting peak analysis only at the predetermined cycles, the quantification of target nucleic acid sequences may be done in more rapid and convenient manner.

(b) In the methods disclosed in U.S. Pat. No. 8,039,215, where melting peak maximum values at certain cycle are greater than a threshold value, the difference between them is not employed for quantification of target nucleic acid sequences. In contrast, all of the height or area values of melting peaks at the predetermined cycles can be employed for quantification of target nucleic acid sequences.

(c) Because the present invention is based on a melting peak analysis using $T_m$ values of duplexes, it is capable of detect and quantify a plurality of target nucleic acid sequences even using a single type of labels in a simultaneous manner.

(d) The present invention permits to relatively quantify target nucleic acid sequence. Furthermore, the present invention can quantify target nucleic acid sequence in an absolute manner by use of a control with known concentration.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Quantification of a Target Nucleic Acid Sequence by Cyclic Melting Curve Analysis Using the Every Melting Peak Obtained We examined whether the cyclic melting curve analysis using the every melting peak obtained allows quantifying a target nucleic acid sequence. PTOCE assay comprising melting analysis was used for the quantification of the target nucleic acid sequence.

Taq DNA polymerase having a 5' nuclease activity was used for the extension of upstream primer and downstream primer, the cleavage of PTO and the extension of PTO fragment. Genomic DNA of *Neisseria gonorrhoeae* (NG) was used as a standard material and a target nucleic acid sequence.

In PTOCE assay of this Example, the presence of the extended strand produced depending on the presence of a target nucleic acid sequence is detected by melting analysis of the extended duplex formed with the extended strand and CTO. Quantity of the extended duplex is proportional to the initial amount of a target nucleic acid sequence. A height or area of a melting curve peak can reflect the quantity of the extended duplex. In this Example, the melting curve analysis is performed at the three pre-determined cycles. The initial amount of a target nucleic acid sequence is estimated using the sum of melting peak heights obtained from the cyclic melting curve analysis.

The PTO and CTO are blocked with a carbon spacer at their 3'-ends to prohibit their extension. CTO is labeled with a quencher molecule (BHQ-1) and a fluorescent reporter molecule (FAM) in its templating portion (SEQ ID NO: 4).

The sequences of upstream primer, downstream primer, PTO, and CTO used in this Example are:

```
NG-F
                                            (SEQ ID NO: 1)
5'-TACGCCTGCTACTTTCACGCTIIIIIGTAATCAGATG-3'

NG-R
                                            (SEQ ID NO: 2)
5'-CAATGGATCGGTATCACTCGCIIIIICGAGCAAGAAC-3'

NG-PTO
                                            (SEQ ID NO: 3)
5'-ACGACGGCTTGGCCCCTCATTGGCGTGTTTCG[C3 spacer]-3'

NG-CTO
                                            (SEQ ID NO: 4)
5'-[BHQ-1]TTTTTTTTTTTTTTCCTCC[T(FAM)]CCTCCTCTGCC
AAGCCGTCGT[C3 Spacer]-3'
(I: Deoxyinosine)
(Underlined letters indicate the 5'-tagging portion of PTO)
```

The standard reaction was conducted in the final volume of 20 μl containing a series amount of genomic DNA of NG (1 ng, 100 pg, 10 pg, 1 pg or 100 fg), 10 pmole of upstream primer (SEQ ID NO: 1), 10 pmole of downstream primer (SEQ ID NO: 2), 5 pmole of PTO (SEQ ID NO: 3), 3 pmole of CTO (SEQ ID NO: 4), and 10 μl of 2× Master Mix [containing 2.5 mM MgCl$_2$, 200 μM of dNTPs and 1.6 units of Taq DNA polymerase (Solgent, Korea)]. Three reaction tubes were prepared for each standard amount. The sample reaction was conducted in the final volume of 20 μl containing certain amount of genomic DNA of NG (1 ng, 10 pg or 100 fg), 10 pmole of upstream primer (SEQ ID NO: 1), 10 pmole of downstream primer (SEQ ID NO: 2), 5 pmole of PTO (SEQ ID NO: 3), 3 pmole of CTO (SEQ ID NO: 4), and 10 μl of 2× Master Mix [containing 2.5 mM MgCl$_2$, 200 μM of dNTPs and 1.6 units of Taq DNA polymerase (Solgent, Korea)].

The tubes containing the reaction mixture were placed in the real-time thermocycler (CFX96, Bio-Rad); the reaction mixture was denatured for 15 min at 95° C. and subjected to 50 cycles of 30 sec at 95° C., 60 sec at 60° C., 30 sec at 72° C. During the reaction, a melting curve was obtained respectively after the cycles at 30th, 40th, and 50th by cooling the reaction mixture to 55° C., holding at 55° C. for 5 min, and heating slowly at 55° C. to 85° C. The fluorescence was measured continuously during the temperature rise to monitor dissociation of double-stranded DNAs. A melting peak was derived from the melting curve data. The heights of the melting peaks obtained at 30th, 40th and 50th cycle were summed up for the quantification. The experimental results are summarized in Tables 1 and 2.

TABLE 1

| | Amount of Standard [1] | | | | | |
|---|---|---|---|---|---|---|
| | 1 ng | 100 pg | 10 pg | 1 pg | 100 fg | NTC [2] |
| Standard value [3] | 1452 | 1218 | 907 | 617 | 483 | 0 |

[1] Standard is a genomic DNA of *Neisseria gonorrhoeae*.
[2] NTC represents No Target Control.
[3] Standard value for each standard amount is obtained by the sum of the heights of the all melting peaks.

TABLE 2

| Sample [1] | 1 | 2 | 3 | NTC [2] |
|---|---|---|---|---|
| Sample value [3] | 1474 | 930 | 521 | 0 |
| Estimated Quantity (X) in a range level | X > 1 ng | 100 pg > X > 10 pg | 1 pg > X > 100 fg | 0 |
| Actual initial amount in sample | 1 ng | 10 pg | 100 fg | 0 |

[1] Sample contains a genomic DNA of *Neisseria gonorrhoeae* as a target sequence.
[2] NTC represents No Target Control.
[3] Sample value for each sample is obtained by the sum of the heights of the all melting peaks.

The standard values for each standard amount in Table 1 were provided from the standard reaction. A minimum value among the sum of the heights obtained from the three copy tubes was chosen as the standard value for the corresponding standard amount.

By using the standard values, the initial quantities of the samples were estimated in a range level as Table 2. The results showed that the estimated amount range for each sample approximately included the actual amount in the samples.

No peaks were detected in the absence of the target nucleic acid.

This result shows that the cyclic melting curve analysis using the all melting peak enables quantification of a target nucleic acid sequence.

Example 2: Quantification of a Target Nucleic Acid Sequence by Cyclic Melting Curve Analysis Using the First Melting Peak We examined whether the cyclic melting curve analysis using the first melting peak allows quantifying a target nucleic acid sequence. PTOCE assay comprising melting analysis was used for the quantification of the target nucleic acid sequence.

The reaction results obtained from Example 1 were used for the quantification by the cyclic melting curve analysis using the first melting peak.

In this Example, "3000", "2000" and "1000" are artificially chosen with considering the expected maximum melting peak height and assigned to the melting peaks obtained at 30th, 40th and 50th cycle, respectively. The cycle where the first melting peak is observed is determined in the reactions. A value for quantification is calculated by the sum of the value assigned to the cycle and the value of the melting peak height at the cycle. The experimental results are summarized in Tables 3 and 4.

TABLE 3

| | Amount of Standard[1] | | | | | |
|---|---|---|---|---|---|---|
| | 1 ng | 100 pg | 10 pg | 1 pg | 100 fg | NTC [2] |
| Standard value [3] | 3159 | 3052 | 2321 | 2098 | 1483 | 0 |

[1] Standard is a genomic DNA of *Neisseria gonorrhoeae*.
[2] NTC represents No Target Control.
[3] Standard value is obtained by the sum of the height of the first melting peak and a value assigned of the cycle where the first melting peak is observed for each standard.

TABLE 4

| | Sample[1] | | | NTC[2] |
|---|---|---|---|---|
| | 1 | 2 | 3 | |
| Sample value[3] | 3161 | 2334 | 1521 | 0 |
| Estimated Quantity (X) in a range level | X > 1 ng | 100 pg > X > 10 pg | 1 pg > X > 100 fg | 0 |
| Actual initial amount in sample | 1 ng | 10 pg | 100 fg | 0 |

[1]Sample contains a genomic DNA of *Neisseria gonorrhoeae*.
[2]NTC represents No Target Control.
[3]Sample value is obtained by the sum of the height of the first melting peak and a value assigned of the cycle where the first melting peak is observed for each sample.

The standard values for each standard amount in Table 3 were provided from the standard reaction. A minimum value among the height of the first melting peak obtained from the three copy tubes was added to the value assigned to the cycle and the standard value for the corresponding standard amount was calculated.

By using the standard values, the initial quantities of the samples were estimated in a range level as Table 4. The results showed that the estimated range for each sample included approximately the actual initial amount in the samples.

No peaks were detected in the absence of the target nucleic acid.

This result shows that the cyclic melting curve analysis using the first melting peak enables quantification of a target nucleic acid sequence.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for quantifying a target nucleic acid sequence in a nucleic acid sample using a melting peak curve, the method comprising:
   (a) amplifying the target nucleic acid sequence in the nucleic acid sample to form a duplex comprising a labeling moiety, the amplifying comprising performing cycles of repeating a series of reactions; wherein the duplex comprises a double stranded amplified target nucleic acid sequence, a duplex formed by hybridization between the target nucleic acid sequence and a probe, or a duplex formed dependent on the existence of the target nucleic acid sequence; wherein the formation of duplex increases in proportion to the amplification of the target nucleic acid sequence; wherein the labeling moiety generates a detectable signal during association or dissociation of the duplex;
   (b) obtaining a melting peak curve for at least two predetermined cycles of step (a) by performing a melting analysis at the predetermined cycles over a range of temperatures in which the detectable signal from the duplex is detected; and
   (c) quantifying the target nucleic acid sequence using the melting peak curve;
wherein the step (c) is performed by one of the following steps of (c-1), (c-2), (c-3) or (c-4):
(c-1) adding maximum height values or maximum area values of the melting peak curves obtained in the step (b) to quantify an initial amount of the target nucleic acid sequence;
(c-2) assigning a reference value to each of the predetermined cycles and adding the reference values of the predetermined cycles at which melting peak curves are observed, such that an initial amount of the target nucleic acid sequence is quantified;
(c-3) assigning a reference value to each of the predetermined cycles and calculating a value for quantifying by use of the reference value of the first predetermined cycle at which a melting peak curve can be observed, such that an initial amount of the target nucleic acid sequence is quantified; or
(c-4) assigning a reference value to each of the predetermined cycles and calculating a value for quantifying by use of (i) the reference value of the first predetermined cycle at which a melting peak curve can be observed and (ii) a maximum height value or maximum area value of the first observable melting peak curve, such that an initial amount of the target nucleic acid sequence is quantified.

2. The method according to claim 1, wherein the labeling moiety of the duplex is a single label linked to a single strand of the duplex, an interactive dual label containing a reporter molecule and a quencher molecule all of which are linked to the same strand of the duplex, an interactive dual label containing a reporter molecule and a quencher molecule one of which is linked to one strand of the duplex and the other is linked to the other strand of the duplex, or an intercalating dye to be intercalated in the duplex.

3. The method according to claim 1, wherein the amplification of the target nucleic acid sequence is accomplished under conditions of changing temperature; wherein the series of reactions comprises hybridization between a primer for amplification and the target nucleic acid sequence or an amplified copy thereof, extension of the primer and dissociation of the resulting extended strand from the target nucleic acid sequence or an amplified copy thereof; and wherein a cycle comprises one round of said hybridization, extension and dissociation.

4. The method according to claim 1, wherein the amplification of the target nucleic acid sequence is accomplished under isothermal conditions, and a cycle consists of an interval of time.

5. The method according to claim 1, wherein the amplification of the target nucleic acid sequence is performed by PCR (polymerase chain reaction), LCR (ligase chain reaction), GLCR (gap filling LCR), Q-beta (Q-beta replicase amplification), SDA (stand displacement amplification), 3SR (self-sustained sequence replication), NASBA (nucleic acid sequence-based amplification), TMA (Transcription-Mediated Amplification) or RCA (Rolling Circle Amplification).

6. The method according to claim 1, wherein the step (c) is performed by (c-1) adding maximum height values or maximum area values of the melting peak curves obtained in the step (b) to quantify an initial amount of the target nucleic acid sequence.

7. The method according to claim 1, wherein the step (c) is performed by (c-2) assigning a reference value to each of the predetermined cycles and adding the reference values of the predetermined cycles at which melting peak curves are observed, such that an initial amount of the target nucleic acid sequence is quantified.

8. The method according to claim 1, wherein the step (c) is performed by (c-3), assigning a reference value to each of the predetermined cycles and calculating a value for quantifying by use of the reference value of the first predetermined cycle at which a melting peak curve can be observed, such that an initial amount of the target nucleic acid sequence is quantified.

9. The method according to claim 1, wherein the step (c) is performed by (c-4) assigning a reference value to each of the predetermined cycles and calculating a value for quantifying by use of (i) the reference value of the first predetermined cycle at which a melting peak curve can be observed and (ii) a maximum height value or maximum area value of the first observable melting peak curve, such that an initial amount of the target nucleic acid sequence is quantified.

10. The method according to claim 1, wherein the reference value and the calculation method of the value for quantifying are determined in the step of (c-4) such that the value for quantifying obtained when the first observable melting peak curve occurs in an earlier predetermined cycle is higher than or the same as the value for quantifying obtained when the first observable melting peak curve occurs in a later predetermined cycle.

11. The method according to claim 1, wherein the quantification of the target nucleic acid sequence further comprises comparing the result obtained for the nucleic acid sample to the result obtained for another nucleic acid sample or to the result obtained for a control sample with a known concentration of the target nucleic acid sequence.

12. The method according to claim 2, wherein the quantification of the target nucleic acid sequence further comprises comparing the result obtained for the nucleic acid sample to the result obtained for another nucleic acid sample or to the result obtained for a control sample with a known concentration of the target nucleic acid sequence.

13. The method according to claim 3, wherein the quantification of the target nucleic acid sequence further comprises comparing the result obtained for the nucleic acid sample to the result obtained for another nucleic acid sample or to the result obtained for a control sample with a known concentration of the target nucleic acid sequence.

14. The method according to claim 4, wherein the quantification of the target nucleic acid sequence further comprises comparing the result obtained for the nucleic acid sample to the result obtained for another nucleic acid sample or to the result obtained for a control sample with a known concentration of the target nucleic acid sequence.

15. The method according to claim 5, wherein the quantification of the target nucleic acid sequence further comprises comparing the result obtained for the nucleic acid sample to the result obtained for another nucleic acid sample or to the result obtained for a control sample with a known concentration of the target nucleic acid sequence.

16. The method according to claim 10, wherein the quantification of the target nucleic acid sequence further comprises comparing the result obtained for the nucleic acid sample to the result obtained for another nucleic acid sample or to the result obtained for a control sample with a known concentration of the target nucleic acid sequence.

* * * * *

SEQUENCE LISTING

```
<160> NUMBER OF SEQ ID NOS: 4

<210> SEQ ID NO 1
<211> LENGTH: 38
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (22)..(27)
<223> OTHER INFORMATION: n is a, c, g, or t

<400> SEQUENCE: 1
tacgcctgct actttcacgc tnnnnnngta atcagatg                              38

<210> SEQ ID NO 2
<211> LENGTH: 37
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (22)..(26)
<223> OTHER INFORMATION: n is a, c, g, or t

<400> SEQUENCE: 2
caatggatcg gtatcactcg cnnnnncgag caagaac                               37

<210> SEQ ID NO 3
<211> LENGTH: 32
<212> TYPE: DNA
<213> ORGANISM: Artificial Sequence
<220> FEATURE:
<223> OTHER INFORMATION: Synthetic sequence

<400> SEQUENCE: 3
acgacggctt ggccctcat tggcgtgttt cg                                     32

<210> SEQ ID NO 4
<211> LENGTH: 42
<212> TYPE: DNA
```

```
<213> ORGANISM: Artificial Sequence
<220> FEATURE:
<223> OTHER INFORMATION: Synthetic sequence

<400> SEQUENCE: 4 ttttttttt tttttcctcc tcctcctctg ccaagccgtc gt                    42
```